United States Patent [19]

Clyburn

[11] Patent Number: 5,800,439
[45] Date of Patent: Sep. 1, 1998

[54] CEMENT INJECTION AND INTRAMEDULLARY CANAL DRYING SYSTEM

[76] Inventor: Terry A. Clyburn, 8945 Longpoint, No. 218, Houston, Tex. 77055

[21] Appl. No.: 857,421

[22] Filed: May 16, 1997

[51] Int. Cl.$^6$ ............................................. A61B 17/56
[52] U.S. Cl. ................................... 606/94; 606/93
[58] Field of Search ........................... 606/94, 93, 92, 606/95, 86

[56] References Cited

U.S. PATENT DOCUMENTS

| | | | |
|---|---|---|---|
| 4,627,434 | 12/1986 | Murray | 606/94 |
| 4,653,487 | 3/1987 | Maale | 606/94 |
| 4,815,454 | 3/1989 | Dozier, Jr. | 606/94 |
| 4,966,601 | 10/1990 | Draenert | 606/92 |
| 4,973,334 | 11/1990 | Ziemann | 606/92 |
| 5,468,245 | 11/1995 | Vargas, III | 606/94 |
| 5,693,099 | 12/1997 | Harle | 623/16 |

*Primary Examiner*—Guy V. Tucker
*Attorney, Agent, or Firm*—Kenneth A. Roddy

[57] ABSTRACT

An apparatus for use with a bone cement injection gun during pressurized injection of bone cement into the intramedullary canal of a bone prepared for implantation of a prosthetic device to facilitate continuous removal of fluid and blood products from, and simultaneous drying of, the interior surfaces of the intramedullary canal. An elongate tubular member having a central bore is installed on the nozzle of a bone cement injection gun and conducts bone cement through its central bore. A fluid flow passageway, isolated from the central bore, extends from the distal end to the proximal end of the tubular member. A fluid inlet at the distal end is connected to a source of vaccum and a porous absorbent pad surrounds a fluid inlet at the distal end of the tubular member. The pad is received in the intramedullary canal and swells when moisture is absorbed. A resilient generally conical-shaped pressurizing plug slidably mounted on the exterior of the tubular member forms a seal on the opening at the proximal end of the intramedullary cavity. Bone cement under pressure is injected through the central bore while fluid is drawn through the absorbent pad and the fluid flow passageway. The tubular member and injector gun are moved axially outward from the intramedullary canal as it is filled with bone cement under pressure, and fluid and blood products are continuously evacuated from the interior of the canal during the injection and pressurization of the bone cement.

6 Claims, 2 Drawing Sheets

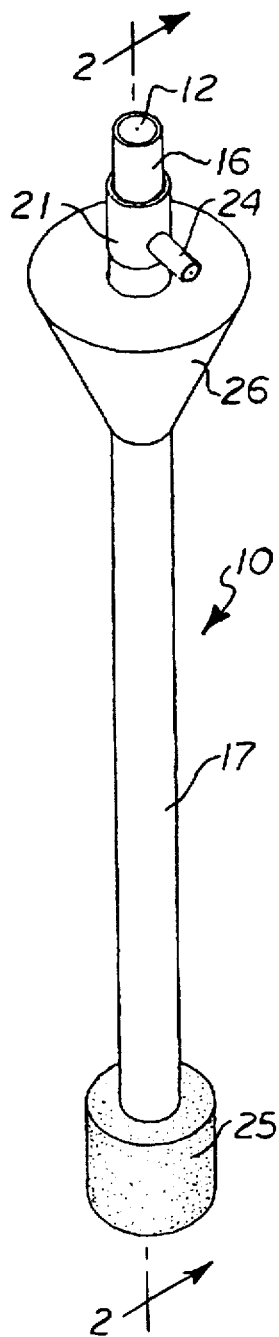
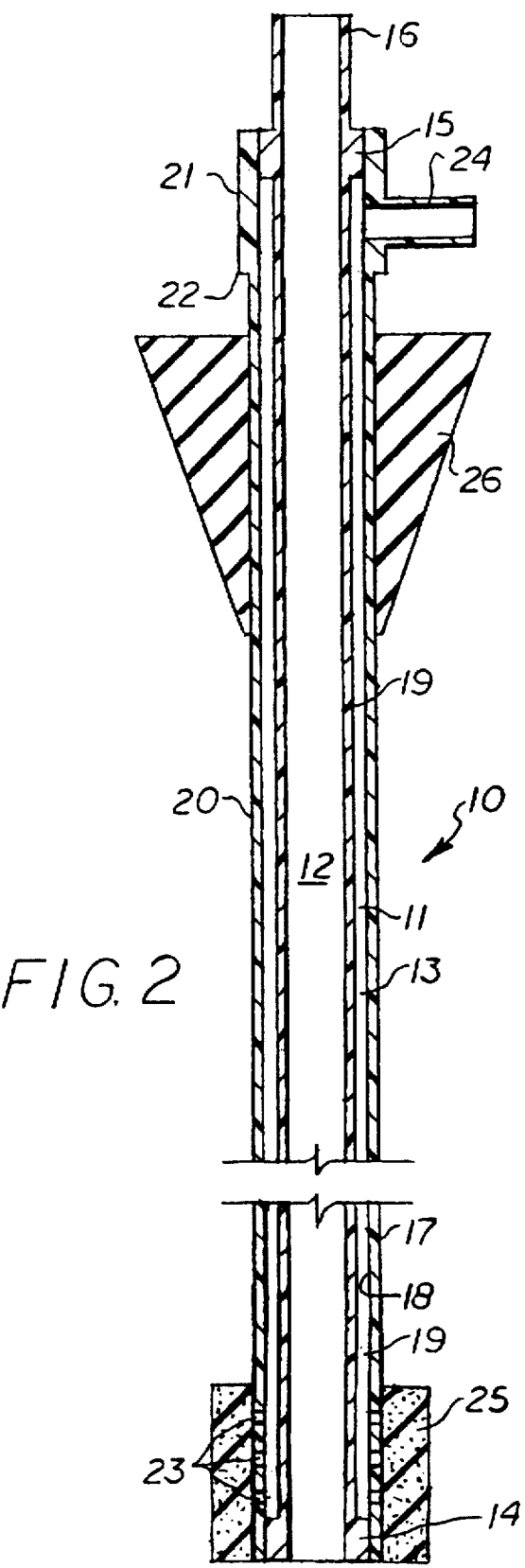

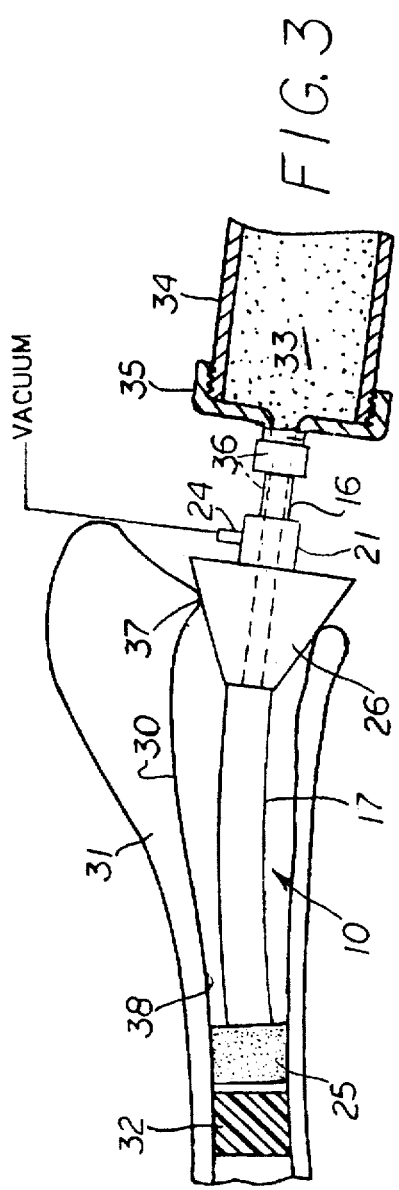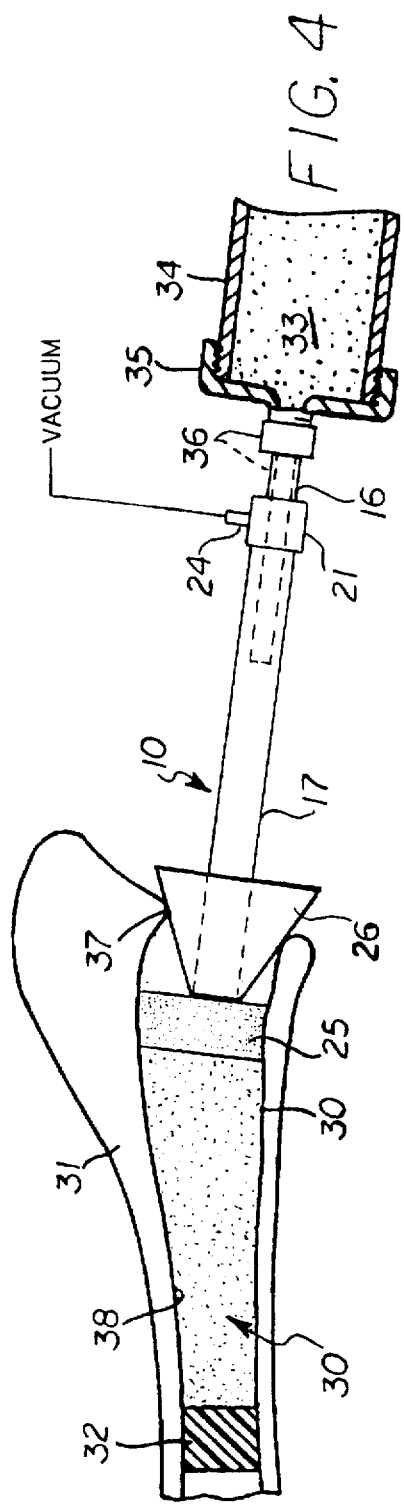

CEMENT INJECTION AND INTRAMEDULLARY CANAL DRYING SYSTEM

BACKGROUND OF THE INVENTION

1. Field of the Invention

This invention relates generally to bone cement injection apparatus and methods, and more particularly to a system for simultaneously drying the intramedullary canal of a bone while injecting bone cement.

2. Brief Description of the Prior Art

Current technology for cemented metallic prosthetic joints into the intramedullary canal of bone has progressed remarkably over the past ten years. The conventional state-of-the-art procedure for cementing metallic prosthetic joints into the intramedullary canal of bone involves the following steps. First, the intramedullary canal is prepared with reamers and rasps to allow for insertion of the prosthesis. A plug is then placed into the intramedullary canal to seal the canal and allow for washing of the canal and to aid in pressurization of the bone cement in the upper canal. The canal is then thoroughly washed using a pressurized fluid delivery system which removes debris of bone, fat, and blood products. Bone cement is then injected into the depths of the canal using a pressurized cement delivery system. A variety of devices are commercially available to contain the cement in the canal and to aid in the pressurization of the bone cement.

Greenwald et al. U.S. Pat. No. 4,294,251 discloses a suction lavage system that incorporates a pulsatile water lavage in combination with a suction system for cleaning out the soft tissue of a bone prior to injecting the bone cement.

Murray, U.S. Pat. No. 4,466,435 discloses an improved cement injection nozzle for use in filling a medullary canal with bone cement that has an expandable shield which scrapes the canal wall and pressurizes the cement as it enters the canal so that it flows into the interstices in the bone.

Noble, U.S. Pat. No. 4,896,662 discloses a pressurizing plug for sealing the opening of the medullary during injection of bone cement.

Draenert, U.S. Pat. No. 4,966,601 discloses a bone cement syringe comprising a container for receiving the bone cement prior to its application and a pressure generating apparatus for precompressing the cement in the container whereby trapped gases are sucked off during precompression to reduce the porosity of the cement which is being applied.

These conventional techniques reduce the amount of fluid and blood in the canal, which results in an improved mechanical bond between the cement and the trabecular bone. Reduced fluid and blood in the canal also results in improved cement strength since there are fewer inclusions of fluid and blood in the cement which often causes stress risers. The pressurization process also improves the density of the cement which results in improved cement strength.

Despite the advantages of these conventional procedures, the problem of the presence of fluid and blood in the boundary between the cement and the bone and the resultant inclusions of fluid and blood in the cement continues to exist. This is due to the fact that even after thorough cleaning and efforts to thoroughly dry the canal, the live bone will continually and actively drain fluids and blood products into the intramedullary canal. Thus, during the time it takes to remove the washing and drying devices and insert the cement injector, a relatively large amount of fluid and blood will build up in the canal and, at the time of cement injection, will mix with the cement.

The present invention is distinguished over the prior art in general, and these patents in particular by an apparatus for use with a bone cement injection gun during pressurized injection of bone cement into the intramedullary canal of a bone prepared for implantation of a prosthetic device to facilitate continuous removal of fluid and blood products from, and simultaneous drying of, the interior surfaces of the intramedullary canal. An elongate tubular member having a central bore is installed on the nozzle of a bone cement injection gun and conducts bone cement through its central bore. A fluid flow passageway, isolated from the central bore, extends from the distal end to the proximal end of the tubular member. A fluid inlet at the distal end is connected to a source of vaccum and a porous absorbent pad surrounds a fluid inlet at the distal end of the tubular member. The pad is received in the intramedullary canal and swells when moisture is absorbed. A resilient generally conical-shaped pressurizing plug slidably mounted on the exterior of the tubular member forms a seal on the opening at the proximal end of the intramedullary cavity. Bone cement under pressure is injected through the central bore while fluid is drawn through the absorbent pad and the fluid flow passageway. The tubular member and injector gun are moved axially outward from the intramedullary canal as it is filled with bone cement under pressure, and fluid and blood products are continuously evacuated from the interior of the canal during the injection and pressurization of the bone cement.

SUMMARY OF THE INVENTION

It is therefore an object of the present invention to provide an apparatus and method to facilitate continuous removal of fluid and blood products from the interior surfaces of the intramedullary canal while simultaneously injecting bone cement into the intramedullary canal of a bone prepared for implantation of a prosthetic device.

It is another object of this invention to provide an apparatus and method to facilitate continuous drying of the interior surfaces of the intramedullary canal while simultaneously injecting bone cement into the intramedullary canal of a bone prepared for implantation of a prosthetic device.

Another object of this invention is to provide an apparatus which will substantially eliminate fluid and blood in the intramedullary canal of a bone during pressurized injection of bone cement and thereby produce an improved mechanical bond between the cement and the trabecular bone.

A further object of this invention is to provide an apparatus which will substantially eliminate stress risers in bone cement due to inclusions of fluid and blood in the cement and thereby produce improved cement bonding of a prosthetic device in the intramedullary canal of a bone.

A still further object of this invention is to provide an apparatus for continuous removal of fluid and blood from and simultaneous drying of the interior surfaces of the intramedullary canal while injecting bone cement into the intramedullary canal of a bone which is simple in construction, inexpensive to manufacture, and rugged and reliable in operation.

Other objects of the invention will become apparent from time to time throughout the specification and claims as hereinafter related.

The above noted objects and other objects of the invention are accomplished by an apparatus for use with a bone cement injection gun during pressurized injection of bone cement into the intramedullary canal of a bone prepared for implantation of a prosthetic device to facilitate continuous removal of fluid and blood products from, and simultaneous drying of, the interior surfaces of the intramedullary canal. An elongate tubular member having a central bore is installed on the nozzle of a bone cement injection gun and conducts bone cement through its central bore. A fluid flow passageway, isolated from the central bore, extends from the distal end to the proximal end of the tubular member. A fluid inlet at the distal end is connected to a source of vaccum and a porous absorbent pad surrounds a fluid inlet at the distal end of the tubular member. The pad is received in the intramedullary canal and swells when moisture is absorbed. A resilient generally conical-shaped pressurizing plug slidably mounted on the exterior of the tubular member forms a seal on the opening at the proximal end of the intramedullary cavity. Bone cement under pressure is injected through the central bore while fluid is drawn through the absorbent pad and the fluid flow passageway. The tubular member and injector gun are moved axially outward from the intramedullary canal as it is filled with bone cement under pressure, and fluid and blood products are continuously evacuated from the interior of the canal during the injection and pressurization of the bone cement.

BRIEF DESCRIPTION OF THE DRAWINGS

FIG. 1 is a perspective view of the apparatus for drying the intramedullary canal of a bone in accordance with the present invention, shown from the proximal end.

FIG. 2 is an enlarged longitudinal cross section through the apparatus for drying the intramedullary canal taken along line 2—2 of FIG. 1.

FIG. 3 is a side elevation view of the apparatus for drying the intramedullary canal installed on the nozzle of a cement injector gun and inserted into the intramedullary canal.

FIG. 4 is a side elevation view showing the apparatus for drying the intramedullary canal and the cement injector gun exiting the intramedullary canal with the absorbent pad in an expanded condition.

DESCRIPTION OF THE PREFERRED EMBODIMENT

Referring to the drawings by numerals of reference, there is shown in FIGS. 1, 2, 3 and 4, a preferred apparatus 10 for drying the intramedullary canal of a bone which has been prepared for implantation of a prosthetic device, such as a metallic joint.

As best seen in FIG. 3, the apparatus 10 has an elongate tubular inner sleeve 11 formed of semi-rigid plastic or other suitable semi-rigid material. The inner sleeve 11 has a central bore 12. The exterior of the inner sleeve 11 has a midsection 13 of a first diameter, and a lower circumferential band or ring 14 formed thereon at its bottom or distal end which is of a larger diameter than the midsection 13, and an upper circumferential band or ring 15 formed thereon at its proximal end which is approximately the same diameter as the lower band or ring 14. The exterior of the upper section 16 of the inner sleeve 11 above the upper band or ring 15 is sized to receive and frictionally engage the exterior of the nozzle of a bone cement injector gun. The inner sleeve 11 is imperforate along its length.

An elongate tubular outer sleeve 17 formed of semi-rigid plastic or other suitable semi-rigid material is secured to the inner sleeve 11. The outer sleeve 17 has a central bore 18 which is sealingly engaged at its lower or distal end on the exterior of the lower band or ring 14 and at its top or proximal end on the exterior of the upper band or ring 15 to define an annulus 19 between the exterior of the midsection 13 of the inner sleeve 11 and the bore 18 of the outer sleeve. The exterior of the outer sleeve 17 has a lower portion 20 of a first diameter which extends upwardly from its bottom end and terminates in a larger diameter top portion 21 at its upper end defining a downwardly facing radial shoulder 22 therebetween.

A plurality of circumferentially spaced fluid inlet holes 23 extend through the side wall of the outer sleeve 17 at its lower end which are disposed above the lower ring or band 14 and in fluid communication with the annulus 19. A tubular hose fitting 24 extends outwardly from the side wall of the top portion 21 of the outer sleeve 17 below the upper ring or band 15 and the radial shoulder 22. The interior of the hose fitting 24 is in fluid communication with the annulus 19. The hose fitting 24 is sized and shaped to receive one end of a conduit or vacuum hose which is connected at its other end to a conventional vacuum source.

A cylindrical pad 25 of porous resilient absorbent material is secured to the lower end of the outer tube 17 and surrounds the fluid inlet holes 23. The exterior diameter of the porous resilient absorbent pad 25 is sized to be received within the interior of the intramedullary canal. The absorbent pad 25 is preferrably formed of a commercially available compressed super absorbent surgical sponge material which will swell or expand when exposed to liquids, such as that used in a product commonly referred in the medical trade as a "surgical tampon". The absorbent pad 25 may also be formed with an outer skin having a smaller pore size than its interior portion to facilitate sliding it along the interior surface of the intermedullary canal of the bone and reduce the likelihood of becoming snagged.

A generally conical-shaped sealing or pressurizing plug 26 formed of resilient material such as rubber is slidably mounted on the exterior of the outer sleeve 17 beneath the radial shoulder 22. The exterior of the sealing or pressurizing plug 26 tapers downwardly and inwardly and terminates at its distal end in a diameter which is smaller than the bone cavity and is sized and shaped such that its exterior will seal the opening at the proximal end of the cavity.

OPERATION

Referring now to FIGS. 3 and 4, the intramedullary canal 30 of the bone 31 is prepared with reamers and rasps to allow for insertion of the prosthesis. A plug 32 is secured at the distal end of the reamed area to seal the canal and the canal is then thoroughly washed using a conventional pressurized fluid delivery system which removes debris of bone, fat, and blood products.

The conventional bone cement injection gun (not shown) is similar to a caulking gun having a handle and a trigger which operates a plunger to extrude penetrating bone cement 33 contained within a cartridge 34 installed in the gun. A front closure cap 35 at the front of the cartridge has a nozzle 36 threadedly connected thereon.

The upper or proximal end 16 of the inner sleeve 11 of the drying apparatus is pressed onto the nozzle 36 of the injector gun. The distal end of the drying apparatus 10 is inserted into the intramedullary canal with the absorbent pad 25 adjacent to the plug 32 at the distal end of the reamed area. The resilient pressurizing plug 26 is pressed into the opening 37 of the canal to seal the proximal end of the canal. The hose fitting 24 is connected to the vacuum source by a conduit and the vacuum is turned on.

Bone cement is then injected through the inner sleeve 11 of the drying apparatus 10 while at the same time, the vacuum is drawing air from the canal through the pad 25 and the annulus 19 between the inner and outer sleeves 11 and 13. As the surgeon injects the cement, the pressure of the cement filling the canal beneath the drying apparatus forces the injector gun along with the drying apparatus to gradually exit the canal.

During this procedure, the drying apparatus 10 continuously and actively dries the canal. As the absorbent pad 25 becomes wet with fluid and blood products, it will swell or expand radially to engage the interior surface 38 of the canal. As the drying apparatus moves toward the proximal end of the canal the expanded absorbent pad 25 slides along the interior surface of the canal. In this manner, the absorbent pad and the vacuum removes fluid and blood products which have build up in the canal during the time interval between removal of the washing and drying devices and insertion of the cement injector, and also continously and actively removes and clears the fluid and blood products which continually drain into the canal from the live bone during the injection and pressurization of the bone cement.

While this invention has been described fully and completely with special emphasis upon a preferred embodiment, it should be understood that within the scope of the appended claims the invention may be practiced otherwise than as specifically described herein.

I claim:

1. An apparatus for use with a bone cement injection gun during pressurized injection of bone cement into the intramedullary canal of a bone prepared for implantation of a prosthetic device to facilitate continuous removal of fluid and blood products from, and simultaneous drying of, the interior surfaces of the intramedullary canal, comprising:

an elongate tubular member having a central bore, a proximal end, and a distal end, said proximal end adapted to be engaged on the nozzle of a bone cement injection gun for conducting bone cement through said central bore;

a fluid flow passageway extending from said distal end to said proximal end isolated from said central bore and having a fluid inlet at said distal end and a fluid outlet at said proximal end adapted for connection to a source of vacuum;

a porous absorbent pad secured to said distal end surrounding said fluid inlet and sized to be received in the intramedullary canal; and a resilient generally conical-shaped pressurizing plug slidably mounted on the exterior of said tubular member sized and shaped to form a seal on the opening at the proximal end of the intramedullary cavity; wherein bone cement under pressure is injected through said central bore while fluid is drawn through said absorbent pad and said fluid flow passageway, said tubular member and said injection gun are moved axially outward from said intramedullary canal as it is filled with bone cement under pressure, and fluid and blood products are continuously evacuated from the interior of said intramedullary canal during the injection and pressurization of the bone cement.

2. The apparatus according to claim 1, wherein said porous absorbent pad is formed of surgical sponge material.

3. The apparatus according to claim 1, wherein said porous absorbent pad is formed of compressed super absorbent surgical sponge material capable of swelling and expanding upon contact with liquids.

4. The apparatus according to claim 1, wherein said porous absorbent pad is formed of porous material having an interior portion of a first pore size and an outer skin of a smaller pore size than said first pore size.

5. The apparatus according to claim 1, wherein said elongate tubular member comprises an elongate inner tubular member having a central bore and an exterior diameter;

a coaxial elongate outer tubular member having a central bore radially spaced from said inner tubular member exterior diameter to define an annulus therebetween, said annulus forming a portion of said fluid flow passageway; and seal means at a distal end and a proximal end of said annulus;

said fluid inlet and said fluid outlet extend through the side wall of said outer tubular member and are disposed between said seal means.

6. A method for continuously removing fluid and blood products from, and simultaneous drying of, the interior surfaces of the intramedullary canal of a bone prepared for implantation of a prosthetic device while injecting bone cement under pressure into the intramedullary canal, comprising the steps of:

attaching onto the nozzle of a bone cement injection gun, an elongate tubular member having a central bore, a fluid flow passageway extending from a distal end to a proximal end isolated from said passageway, a fluid inlet at said distal end surrounded by a porous absorbent pad capable of swelling and expanding upon contact with liquids, a fluid outlet at said proximal end connected to a source of vacuum, and a resilient pressurizing plug slidably mounted on the exterior of said tubular member;

inserting the distal end of said tubular member into the intramedullary canal with said absorbent pad positioned adjacent to a plug at the distal end of the canal;

pressing said pressurizing plug into the opening of the intramedullary canal to seal the proximal end of the canal;

activating said source of vacuum to draw fluids and blood products through said absorbent pad and said fluid flow passageway;

injecting bone cement under pressure from said injection gun through said nozzle and said tubular member central bore;

allowing said absorbent pad to swell and expand to engage the interior surface of the intramedullary canal; and moving said injection gun and said tubular member axially outward from said intramedullary canal as it is filled with bone cement under pressure such that said absorbent pad moves along the interior surface of the canal; whereby fluid and blood products are continuously evacuated from the interior of the intramedullary canal during the injection and pressurization of the bone cement.

* * * * *